United States Patent [19]

Pellico et al.

[11] Patent Number: 5,631,000
[45] Date of Patent: May 20, 1997

[54] ANHYDROUS TOOTH WHITENING GEL

[75] Inventors: Michael A. Pellico; Veronica Sababa, both of Los Angeles, Calif.

[73] Assignee: Laclede Professional Products, Inc., Gardena, Calif.

[21] Appl. No.: 599,364

[22] Filed: Mar. 11, 1996

[51] Int. Cl.$^6$ ................................ A61K 7/16; A61C 5/00
[52] U.S. Cl. ............................................... 424/53; 433/215
[58] Field of Search ............................... 424/50, 53, 54

[56] References Cited

U.S. PATENT DOCUMENTS

| | | | |
|---|---|---|---|
| 5,098,303 | 3/1992 | Fischer | 433/215 |
| 5,234,342 | 8/1993 | Fischer | 433/215 |
| 5,290,566 | 3/1994 | Schow et al. | 424/488 |
| 5,376,006 | 12/1994 | Fischer | 433/215 |
| 5,401,495 | 3/1995 | Murayama et al. | 424/53 |
| 5,409,631 | 4/1995 | Fischer | 252/186.25 |
| 5,500,207 | 3/1996 | Goulet | 424/54 |

*Primary Examiner*—Peter F. Kulkosky
*Attorney, Agent, or Firm*—Donald Diamond

[57] ABSTRACT

An anhydrous dental bleaching gel composition is provided which has improved package stability, improved rheology and reduced sensitivity during use. An illustrative anhydrous dental bleaching gel composition embodying these features comprises propylene glycol, polyethylene glycol, glycerin in an amount not exceeding about 10 wt. %, neutralized carboxypolymethylene, hydroxypropylcellulose, and carbamide peroxide.

20 Claims, No Drawings

ANHYDROUS TOOTH WHITENING GEL

FIELD OF THE INVENTION

This invention relates to dental compositions and, more particularly, to anhydrous tooth whitening gel compositions, a method for preparing the gel compositions, and a method for utilizing the gel compositions.

PRIOR ART

In that aspect of aesthetic dentistry which relates to self-administered use of in-home tooth whitening compositions, the dental patient is provided with a custom-fitted dental tray having selectively enlarged tooth treating compartments which are adapted to receive a whitening gel that is dispensed from a syringe. The dental tray, with its gel content, is unobtrusively and advantageously worn by the patient at night and while the patient sleeps. This treatment is repeated for a sufficient period of time to effect the tooth bleaching and whitening process.

It is disclosed in the prior art that carboxypolymethylene as well as methylcelluose can be used as the gelation agents in the formulation of tooth whitening gels. The prior art also discloses that carbamide peroxide (urea peroxide) as well as hydrogen peroxide can be used as the whitening agents in the formulation of tooth whitening gels.

U.S. Pat. No. 5,290,566 (Schow, et al., 1994) discloses a tooth whitening gel containing urea peroxide (carbamide peroxide), methylcelluose and water wherein the concentration of urea peroxide is from about 22 to about 32 wt. %.

U.S. Pat. No. 5,098,303 (Fischer, 1992), U.S. Pat. No. 5,234,342 (Fischer, 1993), U.S. Pat. No. 5,376,006 (Fischer, 1994) and U.S. Pat. No. 5,409,631 (Fischer, 1995), which are incorporated herein by reference, disclose tooth bleaching and whitening gel compositions formulated with carbamide peroxide, water, glycerin, carboxypolymethylene and sodium hydroxide. With respect to broad range ingredient concentration, the formulations contain from about 3.0 to about 20 wt. % carbamide peroxide, from about 10 to about 60 wt. % water, from about 20 to about 70 wt. % glycerin, from about 3.5 to about 12 wt. % carboxypolymethylene and sodium hydroxide in an amount to substantially neutralize the carboxypolymethylene. The gel is characterized as comprising a saturated or super saturated carboxypolymethylene composition wherein the actual concentration of carboxypolymethylene in the total quantity of water in the gel composition is in the range from about 15% to about 40%, with the concentrated carboxypolymethylene providing the gel composition with a tackiness or stickiness. As to gel preparation, the patentee recommends that the carboxypolymethylene be mixed with glycerin and the resulting admixture dispersed in water, followed by the addition of the remaining ingredients, namely, sodium hydroxide and carbamide peroxide.

It has been observed that carbamide peroxide tooth whitening gels containing relatively high concentrations of water, glycerin and carboxypolymethylene (a) tend to have limited package stability as a result of the interaction of carbamide peroxide with water, (b) tend to increase tooth sensitivity as a result of the hygroscopic properties of glycerin which can reduce the moisture level at the tooth treatment surface, and (c) tend to string from one tooth treating compartment in the bleaching tray to the next tooth treating compartment in the tray in the course of syringe loading the compartments with the bleaching gel.

SUMMARY OF THE INVENTION

An important object of the present invention is to provide new and improved dental whitening compositions which address the limitations of the prior art dental bleaching gels as hereinabove described.

Another object of this invention is to provide dental whitening compositions which have improved package stability with respect to the active bleaching agent, namely, the peroxide constituent.

A further object of this invention is to provide dental whitening compositions which have reduced sensitivity during use.

An additional object of this invention is to provide dental whitening compositions which have improved thixotropic properties with respect to flow-set characteristics.

These and other objects and features of the present invention are accomplished with the compositions, methods and procedures as described herein.

In accordance with one aspect of this invention, there is provided a dental whitening composition containing carbamide peroxide dispersed in a substantially anhydrous gelatinous carrier. The anhydrous carrier comprises a liquid component wherein glycerin, if present, is limited to an amount that does not exceed about 10 wt. % based on the total weight of the composition. The anhydrous carrier also comprises a thickener component containing neutralized carboxypolymethylene and cellulosic ether soluble in the liquid component.

In accordance with a second aspect of this invention, there is provided a method for whitening teeth which comprises (1) extruding a substantially anhydrous dental bleaching gel composition into the reservoir system of a dental bleaching tray, (2) placing the dental tray in the oral cavity so as to bring the gel composition into contact with the teeth to be whitened, (3) maintaining the gel composition in contact with the aforesaid teeth for a plurality of hours per day, and (4) repeating steps 1, 2 and 3 for multiple days to effect whitening of the teeth. The anhydrous dental bleaching gel composition which can be used in carrying out the method advantageously comprises (a) propylene glycol in an amount from about 10 wt. % to about 50 wt. %, (b) polyethylene glycol in an amount from about 10 wt. % to about 55 wt. %, and having a molecular weight from about 400 to about 1500, (c) glycerin in an amount from about 0 wt. % to about 10 wt. %, (d) carboxypolymethylene in an amount from about 0.5 wt. % to about 3.0 wt. %, (e) hydroxypropylcellulose in an amount from about 0.5 wt. % to about 10 wt. %, (f) neutralizing reagent in an amount to substantially neutralize carboxypolymethylene, and (g) carbamide peroxide in an amount from about 5.0 wt. % to about 25 wt. %.

In accordance with a third aspect of this invention, there is provided a method for preparing substantially anhydrous dental whitening gel compositions. The method comprises admixing a settable ingredient mix to obtain a homogenous dispersion of the ingredients. The settable ingredient mix advantageously comprises (a) propylene glycol in an amount from about 10 wt. % to about 55 wt. %, (b) polyethylene glycol in an amount from about 10 wt. % to about 50 wt. %, and having a molecular weight from about 400 to about 1500, (c) glycerin in an amount from about 0 wt. % to about 10 wt. %, (d) carboxypolymethylene in an amount from about 0.5 wt % to about 3.0 wt. % (e) hydroxypropylcellulose in an amount from about 0.5 wt. % to about 10 wt. %, (f) neutralizing reagent in an amount to substantially neutralize carboxypolymethylene, and (g) carbamide peroxide

DETAILED DESCRIPTION

The dental whitening gel compositions of this invention comprise carbamide peroxide dispersed in an anhydrous gelatinous carrier. Carbamide peroxide is generally present in the anhydrous gel compositions in an amount from about 5 wt. % to about 25 wt. % and, preferably, in an amount from about 10 wt. % to about 20 wt. %.

The anhydrous gelatinous carrier comprises a liquid component and a thickener component. Liquid polyols such as propylene glycol and polyethylene glycol are advantageously used in formulating the liquid component. Propylene glycol is generally present in the gel compositions in an amount from about 10 wt. % to about 55 wt. % and, preferably, in an amount from about 25 wt. % to about 45 wt. %. Polyethylene glycol which can be used in the practice of this invention has a molecular weight from about 400 to about 1500 and is generally present in the gel compositions in an amount from about 10 wt. % to about 50 wt. % and, preferably, in an amount from about 25 wt. % to about 45 wt. %.

Glycerin can also be used as a constituent of the liquid component. However, glycerin is hygroscopic and a high concentration of glycerine in the gel tends to pull moisture away from the surface of the teeth which can lead to increased dental sensitivity to the bleaching composition. Accordingly, if glycerin is used in the bleaching gel, it should be limited to a concentration that does not exceed about 10 wt. % of the gel composition. In a more specific aspect, glycerin can be present in the gel composition in an amount from about 3.0 wt. % to about 9.0 wt. %.

The thickener portion of the gel composition advantageously contains a blend of neutralized carboxypolymethylene and cellulosic ether that is soluble in the liquid component. Carboxypolymethylene is generally present in the gel compositions in an amount from about 0.5 wt. % to about 3.0 wt. % and, preferably, in an amount from about 1.5 wt. % to about 2.5 wt. %. Carboxypolymethylene is characterized as a slightly acidic vinyl polymer with active carboxyl groups. Typically, the acidic carboxypolymethylene is neutralized in situ during the preparation of the gel composition by adding an anhydrous alkalinizing agent such as anhydrous sodium hydroxide to the pre-gelatinous mix in order to bring the pH of the gel composition to an orally acceptable level as, for example, a pH from about 6.0 to about 7.5.

Cellulosic ether is generally present in the gel compositions in an amount from about 0.5 wt. % to about 10 wt. % and, preferably, in an amount from about 1.0 wt. % to about 3.0 wt. %. A preferred cellulosic ether is hydroxypropylcellulose.

The blend of neutralized carboxypolymethylene and cellulosic ether is particularly advantageous because the blend provides the gel compositions with improved thixotropic properties in respect of flow-set characteristics. This rheological enhancement constitutes an improvement in the dental bleaching art because it tends to minimize the stringing and roping of the gel from one tooth treating compartment to the next tooth treating compartment during the sequential syringe loading of the gel into the compartments of the dental bleaching tray.

The anhydrous dental bleaching gels of this invention are prepared by adding and mixing the ingredients of the formulation in a suitable vessel such as a stainless steel tank that is provided with a heavy duty mixer which is suitable for use with thick gels. If desired, the mixing vessel can be combined with vacuum equipment for carrying out the admixing of the ingredients under vacuum conditions. The ingredients of the formulation are mixed to obtain a homogenous dispersion which sets to a thixotropic gel.

In the preparation of the dental whitening gels, the formulating ingredients are advantageously added to the mixing vessel in the following order: liquid ingredients, thickener ingredients, alkalinizing agent, carbamide peroxide, and any desired flavoring.

The quantities of the formulating ingredients are so selective as to provide the whitening gels with a composition containing (a) propylene glycol in an amount from about 10 wt. % to about 55 wt. % and, preferably, in an amount from about 25 wt % to about 45 wt. %, (b) polyethylene glycol in an amount from about 10 wt. % to about 50 wt. % and, preferably, in am amount from about 25 wt. % to about 45 wt. % and having a molecular weight from about 400 to about 1500, (c) glycerin in an amount from about 0 wt. % to about 10 wt. % and, preferably, in an amount from about 3.0 wt. % to about 9.0 wt. %, (d) carboxypolymethylene in an amount from about 0.5 wt. % to about 3.0 wt. % and, preferably, in an amount from about 1.5 wt. % to about 2.5 wt. %, (e) hydroxypropylcellulose in an amount from about 0.5 wt. % to about 10 wt. % and, preferably, in an amount from about 1.0 wt. % to about 3.0 wt. %, (f) neutralizing reagent, preferably, anhydrous sodium hydroxide in an amount to substantially neutralize carboxypolymethylene, and (g) carbamide peroxide in an amount from about 5.0 wt. % to about 25 wt. % and, preferably, in an amount from about 10 wt. % to about 20 wt. %.

EXAMPLES

The following examples further illustrate the anhydrous dental bleaching gels of this invention and the concentration ranges for the ingredients thereof. As used in the examples, "PEG" is a trade designation for polyethylene glycol (Merck Index No. 7545, 11th ed.), "Carbopol" is a trademark for carboxypolymethylene (Merck Index No. 1836, 11th ed.) and "Klucel" is a trademark for hydroxypropylcellulose (Merck Index No. 4776, 11th ed.). The bleaching gels were prepared in accordance with the method and procedure as hereinabove described.

| Ingredients | Weight Percent | | | | |
|---|---|---|---|---|---|
| | Ex. 1 | Ex. 2 | Ex. 3 | Ex. 4 | Ex. 5 |
| Propylene glycol | 47.4 | 49.0 | 45.4 | 43.4 | 48.4 |
| PEG 600 | 20.0 | 21.7 | — | 16.0 | 15.0 |
| PEG 1000 | 10.0 | 11.7 | — | — | 15.0 |
| PEG 1450 | — | — | 26.0 | 6.0 | — |
| PEG 1500 | — | — | — | — | — |
| Glycerin | 8.0 | 8.0 | 8.0 | 8.0 | 7.0 |
| Carbopol 980 | 2.2 | 2.2 | 2.2 | 2.2 | 2.2 |
| Klucel GFF | 1.8 | 1.8 | 1.8 | 1.8 | 1.8 |
| Flavor | 0.2 | 0.2 | 0.2 | 0.2 | 0.2 |
| Sodium hydroxide | 0.4 | 0.4 | 0.4 | 0.4 | 0.4 |
| Carbamide peroxide | 10.0 | 5.0 | 16.0 | 22.0 | 10.0 |
| | 100.0 | 100.0 | 100.0 | 100.0 | 100.0 |

| Ingredients | Weight Percent | | | |
| --- | --- | --- | --- | --- |
| | Ex. 6 | Ex. 7 | Ex. 8 | Ex. 9 |
| Propylene glycol | 46.4 | 45.4 | 54.2 | 41.1 |
| PEG 600 | — | — | 28.0 | — |
| PEG 1000 | 31.0 | 16.0 | — | — |
| PEG 1450 | — | 16.0 | — | — |
| PEG 1500 | — | — | — | 35.2 |
| Glycerin | 8.0 | 8.0 | 3.0 | 3.0 |
| Carbopol 980 | 2.2 | 2.2 | 2.0 | 3.0 |
| Klucel GFF | 1.8 | 1.8 | 0.4 | 1.0 |
| Klucel MFF | — | — | 0.8 | — |
| Flavor | 0.2 | 0.2 | 0.2 | 0.2 |
| Sodium hydroxide | 0.4 | 0.4 | 0.4 | 0.5 |
| Carbamide peroxide | 10.0 | 10.0 | 11.0 | 16.0 |
| | 100.0 | 100.0 | 100.0 | 100.0 |

The anhydrous dental whitening gel compositions, as hereinabove described, are packaged in appropriate syringes for dispensing into custom-fitted dental trays that are usually worn at night, but can also be worn during the day, with maximum whitening generally occurring when the treatment is continued for ten to fourteen days. The custom-fitted dental bleaching trays can be prepared by using materials and procedures that are well known in the dental art, and which are described in the prior art cited herein.

In a first alternative packaging embodiment, the dental whitening gels can be packaged in gel dispensing tubes or bottles for extrusion into general purpose dental trays for carrying out the dental whitening process. In a second alternative packaging embodiment, pre-packaged dental trays can be provided to the user containing dental whitening gels which have been adapted for this purpose.

In view of the foregoing descriptions and examples, it will become apparent to those of ordinary skill in the art that equivalent modifications thereof may be made without departing from the spirit and scope of this invention.

That which is claimed is:

1. An anhydrous tooth whitening gel composition comprising carbamide peroxide dispersed in an anhydrous gelatinous carrier, said carrier comprising:
   (a) a liquid polyol wherein glycerin, if present, is limited to an amount that does not exceed about 10 wt. % based on the total weight of the composition; and
   (b) a thickener component containing neutralized carboxypolymethylene and cellulosic ether soluble in the liquid component, said anhydrous tooth whitening gel composition having enhanced package stability, reduced tooth sensitivity, and improved thixotropic properties.

2. The composition of claim 1 wherein the liquid component includes propylene glycol in an amount from about 10 wt. % to about 55 wt. % based on the total weight of the composition and polyethylene glycol in an amount from about 10 wt. % to about 50 wt. % based on the total weight of the composition, said polyethylene glycol having a molecular wt. from about 400 to about 1500.

3. The composition of claim 1 wherein glycerin is present in an amount from about 3.0 wt. % to about 9.0 wt. %.

4. The thickener of claim 1 wherein the cellulosic ether is hydroxypropylcelluose in an amount from about 0.5 wt. % to about 10 wt. % based on the total weight of the composition and the concentration of carboxypolymethylene in the composition is from about 0.5 wt. % to about 3.0 wt. %.

5. The composition of claim 1 wherein the concentration of carbamide peroxide is from about 5.0 wt. % to about 25 wt. %.

6. An anhydrous tooth whitening gel composition comprising:
   (a) propylene glycol in an amount from about 10 wt. % to about 55 wt. %,
   (b) polyethylene glycol in an amount from about 10 wt. % to about 50 wt. %, and having a molecular weight from about 400 to about 1500,
   (c) glycerin in an amount from about 0 wt. % to about 10 wt. %,
   (d) carboxypolymethylene in an amount from about 0.5 wt. % to about 3.0 wt. %,
   (e) hydroxypropylcellulose in an amount from about 0.5 wt. % to about 10 wt. %,
   (f) neutralizing reagent in an amount to substantially neutralize carboxypolymethylene, and
   (g) carbamide peroxide in an amount from about 5.0 wt. % to about 25 wt. %, said anhydrous tooth whitening gel composition having enhanced package stability, reduced tooth sensitivity, and improved thixotropic properties.

7. The composition of claim 6 wherein propylene glycol is present in an amount from about 25 wt. % to about 45 wt. %.

8. The composition of claim 6 wherein polyethylene glycol is present in an amount from about 25 wt. % to about 45 wt. %.

9. The composition of claim 6 wherein glycerin is present in an amount from about 3.0 wt. % to about 9.0 wt. %.

10. The composition of claim 6 wherein carboxypolymethylene is present in an amount from about 1.5 wt. % to about 2.5 wt. %.

11. The composition of claim 6 wherein hydroxypropylcellulose is present in an amount from about 1.0 wt. % to about 3.0 wt. %.

12. The composition of claim 6 wherein carbamide peroxide is present in an amount from about 10 wt. % to about 20 wt. %.

13. A method for whitening teeth which comprises:
   (1) extruding an anhydrous tooth whitening gel composition into the reservoir system of a tooth bleaching dental tray, said gel composition comprising:
      (a) propylene glycol in an amount from about 10 wt. % to about 55 wt. %,
      (b) polyethylene glycol in an amount from about 10 wt. % to about 50 wt. %, and having a molecular weight from about 400 to about 1500,
      (c) glycerin in an amount from about 0 wt. % to about 10 wt. %,
      (d) carboxypolymethylene in an amount from about 0.5 wt. % to about 3.0 wt. %,
      (e) hydroxypropylcellulose in an amount from about 0.5 wt. % to about 10 wt. %,
      (f) neutralizing reagent in an amount to substantially neutralize carboxypolymethylene, and
      (g) carbamide peroxide in an amount from about 5.0 wt. % to about 25 wt. %;
   (2) placing said dental tray in the oral cavity so as to bring the gel composition into contact with the teeth to be whitened;
   (3) maintaining said gel composition in contact with said teeth for a plurality of hours per day; and
   (4) repeating steps 1, 2 and 3 for multiple days to thereby whiten the teeth, said anhydrous tooth whitening gel composition having enhanced package stability, reduced tooth sensitivity, and improved thixotropic properties.

14. The method of claim 13 wherein glycerin is present in the gel composition in an amount from about 3.0 wt. % to about 9.0 wt. %.

15. The method of claim 13 wherein carboxypolymethylene is present in the gel composition in an amount from about 1.5 wt. % to about 2.5 wt. %.

16. The method of claim 13 wherein hydroxypropylcellulose is present in the gel composition in an amount from about 1.0 wt. % to about 3.0 wt. %.

17. A method for preparing an anhydrous tooth whitening gel composition, which method comprises admixing:

(a) propylene glycol in an amount from about 10 wt. % to about 55 wt. %, (b) polyethylene glycol in an amount from about 10 wt. % to about 50 wt. %, (c) glycerin in an amount from about 0 wt. % to about 10 wt. %, (d) carboxypolymethylene in an amount from about 0.5 wt. % to about 3.0 wt. %, (e) hydroxypropylcellulose in an amount from about 0.5 wt. % to about 10 wt. %, (f) neutralizing reagent in an amount to substantially neutralize carboxypolymethylene, and (g) carbamide peroxide in an amount from about 5.0 wt. % to about 25 wt. %, (h) wherein weight percent is based on the total weight of the gel composition, said anhydrous tooth whitening gel composition having enhanced package stability, reduced tooth sensitivity, and improved thixotropic properties.

18. The method of claim 17 wherein the amount of glycerin is from about 3.0 wt. % to about 9.0 wt. %.

19. The method of claim 17 wherein the amount of carboxypolymethylene is from about 1.5 wt. % to about 2.5 wt. % and the amount of hydroxypropylcellulose is from about 1.0 wt. % to about 3.0 wt. %.

20. The method of claim 17 wherein said admixing is carried out under vacuum conditions.

* * * * *